(12) United States Patent
Schlensog

(10) Patent No.: US 6,461,324 B1
(45) Date of Patent: Oct. 8, 2002

(54) SUCTION BELL FOR BREAST PUMP

(76) Inventor: Klaus Schlensog, Weidstrasse 5b, CH-6331, Hünenberg (CH)

( * ) Notice: Subject to any disclaimer, the term of this patent is extended or adjusted under 35 U.S.C. 154(b) by 0 days.

(21) Appl. No.: 09/518,887

(22) Filed: Mar. 6, 2000

Related U.S. Application Data

(63) Continuation-in-part of application No. PCT/EP99/01446, filed on Mar. 5, 1999.

(51) Int. Cl.$^7$ .................................. A61M 1/06
(52) U.S. Cl. ........................................ 604/74
(58) Field of Search ....................... 604/73–76, 35, 604/36, 118, 119, 133, 313–316, 323, 326, 346; 119/14.01, 14.22–14.25, 14.31, 14.32, 14.46–14.49

(56) References Cited

U.S. PATENT DOCUMENTS

| | | | | |
|---|---|---|---|---|
| 2,542,505 A | | 2/1951 | Gascoigne | 128/281 |
| 2,670,709 A | | 3/1954 | Stampen | 119/14.52 |
| 4,263,912 A | | 4/1981 | Adams | 128/281 |
| 4,323,067 A | | 4/1982 | Adams | 128/281 |
| 4,483,272 A | * | 11/1984 | Tonelli | 119/14.32 |
| 4,799,922 A | | 1/1989 | Beer et al. | 604/74 |
| 5,007,899 A | | 4/1991 | Larsson | 604/74 |
| 5,049,126 A | | 9/1991 | Larsson | 604/74 |
| 5,100,406 A | | 3/1992 | Panchula | 604/74 |
| 5,720,722 A | | 2/1998 | Lockridge | 604/74 |
| 5,885,246 A | | 3/1999 | Ford | 604/74 |
| 5,941,847 A | | 8/1999 | Huber et al. | 604/74 |
| 6,058,879 A | * | 5/2000 | Miefalk | 119/14.47 |

FOREIGN PATENT DOCUMENTS

| | | |
|---|---|---|
| EP | 0 466 462 A | 1/1992 |
| FR | 1067421 | 6/1954 |
| GB | 1161118 | 8/1969 |

* cited by examiner

Primary Examiner—Michael J. Hayes
(74) Attorney, Agent, or Firm—Marshall, Gerstein & Borun

(57) ABSTRACT

A suction bell assembly, and an elastomeric liner therefor, are disclosed in which the bell includes a rigid outer shell (10,310) of generally Y-shaped axial cross section with a conical top portion (101) and a cylindrical body portion (106). A thin, flexible, elastic liner (11) is disposed within the shell and has a conical and preferably corrugated upper portion (111) disposed within the conical top portion of the shell and a peripheral lip (114) for sealingly engaging a rim (19) extending about the shell's top portion. The liner also includes an elongated tubular portion 112 spaced normally inwardly from the shell's inner surface, the tubular portion including a resilient annular flange (119) that sealingly engages a shoulder at the lower end of the shell to maintain the liner in an axially stretched and tensioned state. one-way valve means (13,43) is formed integrally with the liner and is disposed at the lower end of the tubular portion below the flange (119). The valve means (13,43) includes a calotte-shaped closure portion (131) having at least one slit (28, 438,439) to permit the passage of milk downwardly through the lower end of the liner. In preferred embodiments, each slit (28,438,439) has offset but communicating inner and outer portions (28$a$,28$b$,438$a$,438$b$, 439$a$,439$b$). Means are also disclosed for allowing swivel action of the shell (310) in relation to a connector (32) for detachably connecting the suction bell to a milk-collecting bottle.

22 Claims, 4 Drawing Sheets

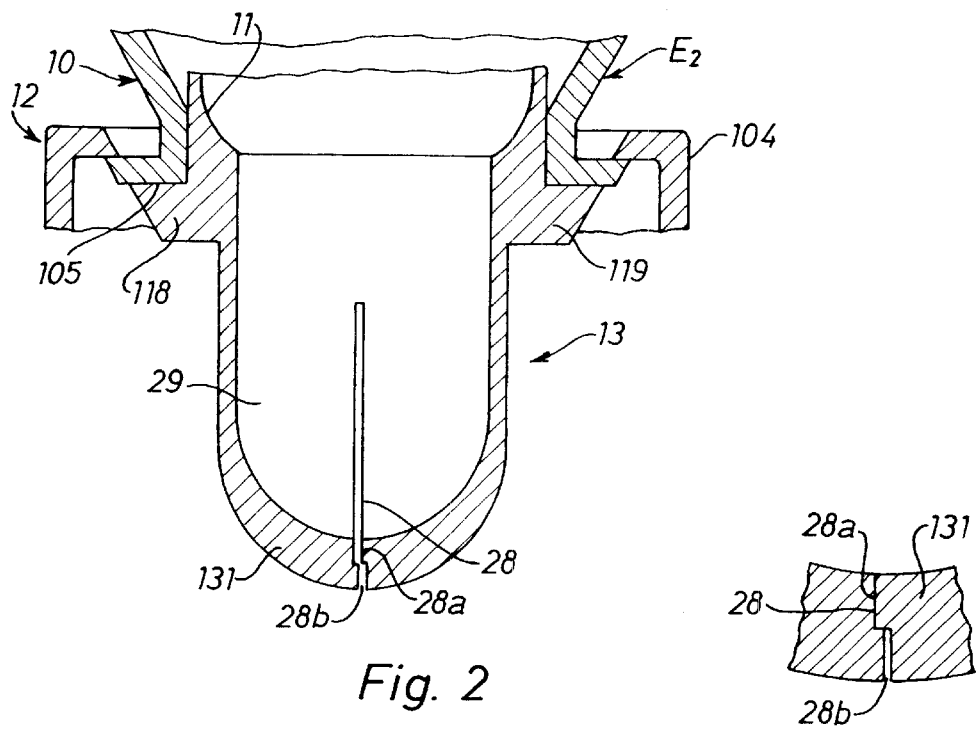
Fig. 2
Fig. 2A
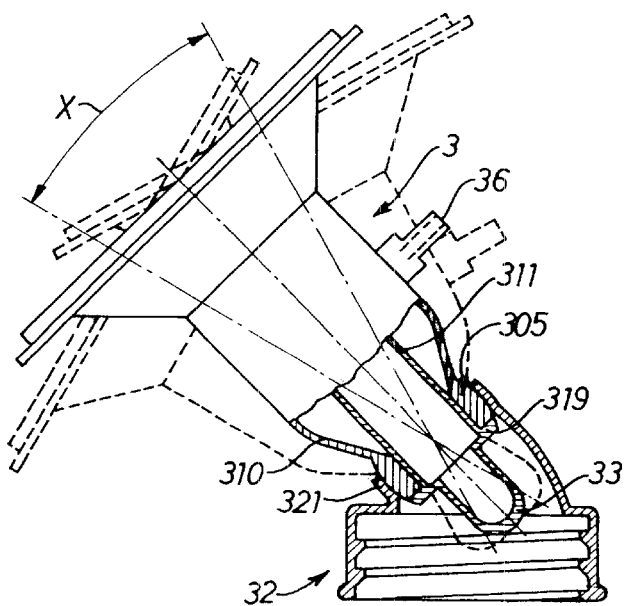
Fig. 3

SUCTION BELL FOR BREAST PUMP

RELATED APPLICATION

This is a continuation-in-part of International Application PCT/EP99/01446 with an international filing date of Mar. 5, 1999.

FIELD OF THE INVENTION

The present invention generally relates to the collection of breast milk and specifically to an improved suction bell for a breast pump and to an insert or liner for such a suction bell.

PRIOR ART

Breast pumps of various designs have been known since early in the twentieth century and a large number of patents relating to that subject matter have issued since. Common features of such devices are a generally flared member (commonly termed a "suction bell") adapted to encompass the nipple region of a mother's breast, a source of cyclic sub-atmospheric pressure (also termed a suction device or pump), and milk collecting means usually in the form of a bottle.

Obviously, an essential factor, both with regard to a user's comfort as well as to stimulation of the lactation process are the feel of the suction bell when in contact with a breast and the impact of the cyclic pressure changes. In line with these requirements, U.S. Pat. No. 2,542,505 (to G. H. Gascoigne) discloses a shell made of metal and consisting of a recessed disc-like head connected with a conical body provided with a central hub, and an elastic liner connected with the conical body at the liner's upper and lower ends. Two separate inter-spaces are formed between the liner and the shell; a first inter-space is formed between the hub, the disk near its front face, and the liner, and a second inter-space is formed between the liner and the conical portion of the shell's body.

The aim of the the Gascoigne device is to simulate natural actions produced by the facial movements and mouth suction of a suckling baby by pneumatically-produced pulsation. To that end, periodic pressure pulses are applied at the first inter-space while suction pulses are applied both inside the liner as well as inside the second inter-space; in other words, suction pulses are combined weith pressure pulses.

However, the Gascoigne device was not and is not suitable for practical use for a variety of reasons. First, its complicated structure would be costly with regard to production and maintenance. Second, and even more essential for user acceptance, is the virtual impossibility of cleaning and sterilizing the device between uses by normal means available in a household. Other disadvantages result from the need to apply both pressure and suction pulses, requiring three pneumatic lines, one for continuous suction applied inside the liner and acting directly upon the breast, and two pulse lines, one for suction pulses and one for pressure pulses applied outside the liner at different portions thereof.

U.S. Pat. No. 4,263,912 (F. H. Adams) discloses milking devices suitable for both humans and cows. The element common to both embodiments is a flexible liner which, in the case of a breast pump, is disposed within a shell with an inter-space formed between the shell and the liner. Suction is applied periodically to the inter-space. While the structure of the breast pump embodiment is relatively simple, compared with Gascoigne, cleaning and safe sterilization are not easily possible. So, again, this device has not, to the best of applicant's knowledge, been widely accepted, nor has another device disclosed by the same inventor in U.S. Pat. No. 4,323,067 which requires two suction means and where the suction bell is made of an elastic material and integrally forms a membrane-closed suction chamber for periodic suction pulses.

OBJECTS AND SUMMARY OF THE INVENTION

Accordingly, it is an object of the present invention to provide an improved suction bell for a breast pump that avoids the aforementioned drawbacks of prior art suction bells by means of a simple and effective structure for simulating a normal suckling action when operated, and which can be easily assembled and disassembled for cleaning and sterilization by means readily available in the home, that is, by immersion in boiling water.

Another object is to provide a suction bell that meets the above objects yet can be manufactured at low cost.

A still further object is to provide a suction bell that can be used with a variety of breast pumping devices, including electrically-operated pumps and manually-operated pumps.

Yet another object of the invention is to provide an integral or monolithic liner that can be easily mounted in and disassembled from a rigid shell for a suction bell while providing the following advantages: optimum contact with a mother's breast for stimulating the flow of milk and for simulating the mouth action of a nursing infant; smooth withdrawal of milk while preventing direct exposure of the milk to air flowing to and from the pumping means; easy and simple cleaning and sterilization of the liner and shell apart from each other and apart from other components of the breast pump assembly; and low production costs. With respect to the latter, it is a specific object to provide a one-piece liner and valve combination that can molded in its entirety from a suitable elastomeric material with a minimum of processing steps.

Briefly, and according to a first general embodiment, the suction bell comprises a rigid outer shell that is generally funnel-shaped, that is, one that is substantially Y-shaped in longitudinal section, having a conical top portion with an open upper end and a cylindrical body portion with an open lower end. The conical top portion of the shell has an outwardly extending rim at its upper end and the cylindrical body portion has first connecting means for connecting the interior of the shell with a source of cyclic sub-atmospheric pressure such as, for example, a conventional manually- or electrically-operated pump, such as a membrane pump. The lower end of the shell is provided with an annular shoulder and is detachably joined to connecting means for attachment to a standard milk collecting receptacle (bottle).

A thin, flexible elastic liner is detachably mounted within the shell, the liner having a conical upper portion disposed within the conical top portion of the shell and provided with a peripheral lip for sealingly engaging the shell's rim. The liner also includes an elongated tubular portion that extends through the shell's cylindrical body portion and has an outer surface spaced inwardly from the shell's inner surface when the pressure within the cylindrical body portion of the shell is at ambient or atmospheric pressure. The tubular portion of the liner includes a resilient annular flange that sealingly engages the shoulder of the shell so that the liner is held in an axially stretched and tensioned state between its upper and lower connections with the shell. Further, the liner includes an integral one-way valve at the lower end of the liner's tubular portion and below the shoulder of the shell. In a preferred embodiment, the valve has a calotte-shaped end portion with at least one slit that has offset portions extending from opposite inner and outer surfaces, resulting in a one-way valve structure that opens easily to allow the flow of milk, seals effectively when the pressure external to the liner is reduced, and may be inexpensively manufactured with a minimum of production steps. In a further embodiment, the calotte-shaped end portion of the valve has a pair of crossed slits, each with offset portions wich provide the described advantages. The offset of the slit portions allow the slit or slits to be formed at the time the liner is molded rather than in one or more subsequent cutting operations.

The conical upper portion of the liner is provided with a multiplicity of coaxial corrugations for contacting the breast in the area of the nipple, such corrugations promoting effective sealing against the breast without sticking to the skin and tending to spread and contract during operation of a breast pump in a manner that is believed to stimulate and enhance the flow of milk.

In a further embodiment of the invention, the connecting means for joining the rigid funnel-like shell to a collection receptacle (bottle) permits swivel action of the shell to increase user comfort and help insure proper sealing contact between the conical portion of the resilient liner and the user's breast.

Other features, objects and advantages will become apparent from the specification and drawings.

DEFINITION OF TERMS

The term "rigid" as used herein in reference to the structure of the shell is intended to refer in a relative sense to a material that will show no substantial deformation when the bell is exposed to alternating air pressures and other forces in normal use.

The term "upper" (or "upstream") is intended to refer, again in a relative sense, to the flared open end of a Y-shaped (or funnel-shaped) structure oriented so that the single tubular leg of the Y, or the narrowest part of the funnel, is at the "lower" end thereof.

The term "elongated" as used herein refers to a structure that is longer than it is wide, e.g., has a length of at least twice its width.

"Sealing" as used herein refers to the connections between the upper and lower portions of the liner with the upper and lower parts, respectively, of the rigid outer shell and indicates a normally air-tight or hermetic connection.

"Sub-atmospheric pressure" is an absolute pressure that is lower than ambient pressure at the site of use of the invention and is used interchangeably with "suction" or "vacuum." Typical absolute sub-atmospheric pressures for use according to this invention are in the general range of from about 50 to about 500 millibar (mbar) which correspond to relative pressures in the range of minus 950 to minus 500 mbar. The extend of pressure reduction is not considered critical for reasons of the self-limiting effect provided according to the invention; that is, the impact of suction upon the breast is limited by the volume of the space provided for expansion of the elastic liner within the rigid shell.

The term "about" is intended herein to include deviations of a numeric value preceded by this term of ±20% of the value given.

The phrase "a thin, flexible and elastic" material is used herein to define the nature of the liner material and is intended to refer to a soft, organic and preferably synthetic material having a thickness in the range from about 50 to 1000 μm micrometers) and which is capable of being easily folded upon itself without damage and of being stretched at least 20% of its length and fully recovering when the stretching force is removed. Typically, a liner according to the invention will show an essentially linear and reversible stretch of about 20 mm when tensioned by a force of about 700 grams. Obviously, the thickness of the liner may differ between its sealing ends and its breast-contacting central region but can be easily selected by those experienced in the art in view of the required functions as explained in more detail hereinafter.

BRIEF DESCRIPTION OF THE DRAWINGS

FIG. 2 is an enlarged and broken-off sectional view of the closure end of the bell showing the integral one-way valve of the liner shown in FIG. 1.

FIG. 2A is a fragmentary sectional view of the valve structure of FIG. 2 further enlarged to illustrate the valve's closing function.

FIG. 3 is a partially-sectioned side view of a suction bell according to the invention with a swiveling snap-on connection between the shell and the connecting means for attachment to a container.

DETAILED DESCRIPTION OF PREFERRED EMBODIMENTS

Figure 1:
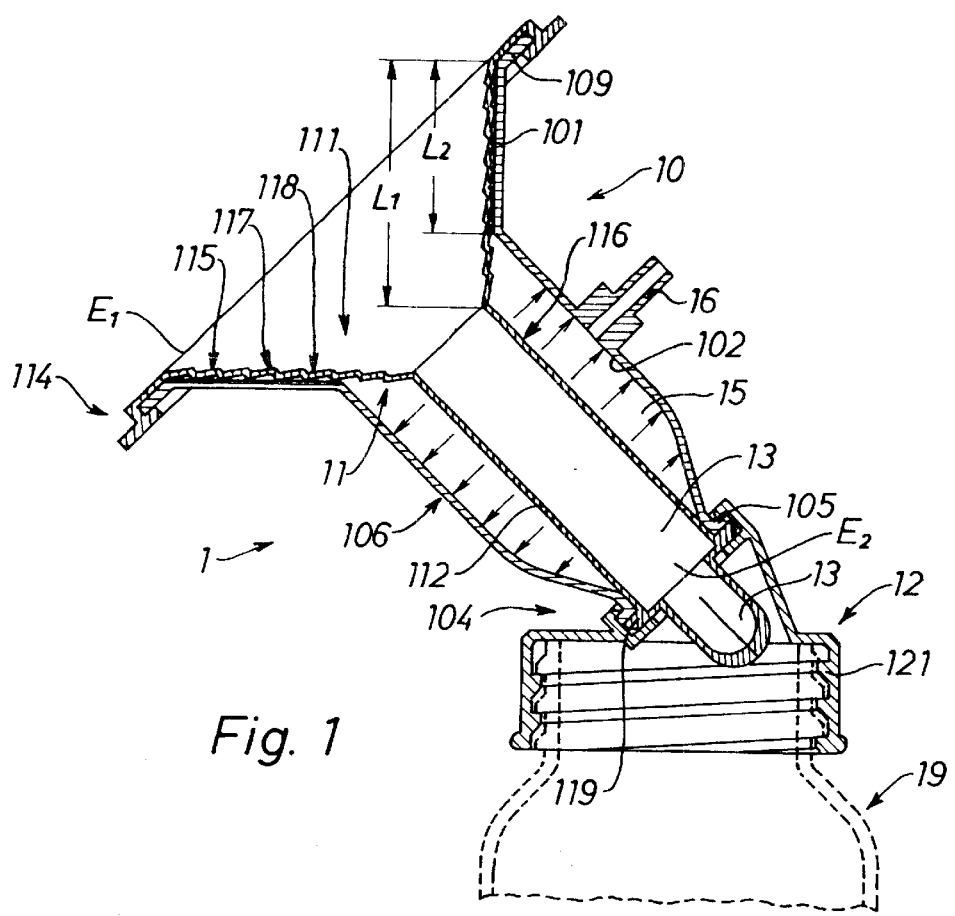
FIG. 1 is a longitudinal sectional view of a suction bell according to the invention.
Figure 1A:
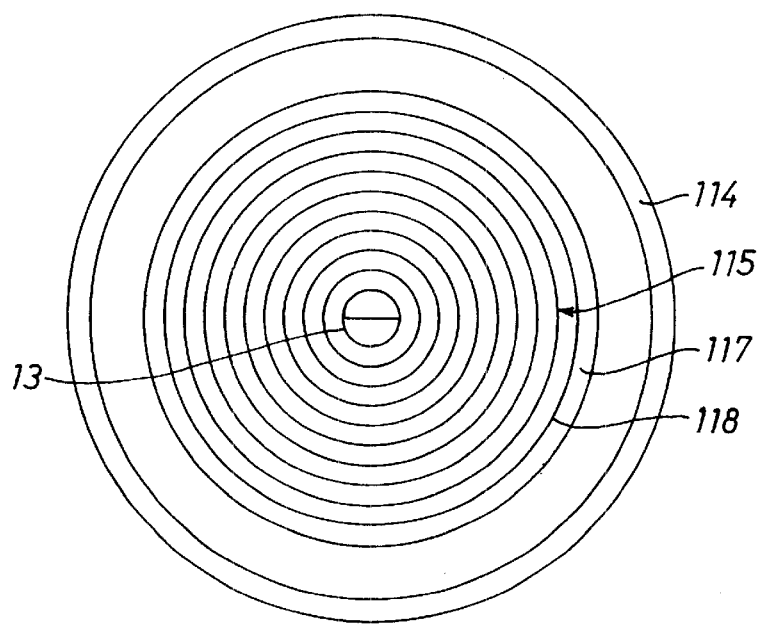
FIG. 1A is a top view of the shell-supported liner of FIG. 1.

The suction bell 1 shown schematically in FIG. 1 in longitudinal section consists essentially of a rigid outer shell 10, liner 11, and connector 12. The suction bell is funnel-shaped and has a substantially Y-shaped cross section as depicted in FIG. 1. The shell has a conical top portion 101 with an open upper end $E_1$ and a cylindrical body portion 106 with an open lower end $E_2$. At its open upper end $E_1$, top portion 101 of the shell is provided with a rim 109 for a sealable yet easily mountable and removable snap-connection with the peripheral lip 114 of the liner which wraps about the rim. The angular position of rim 109 relative to conical top portion 101, with the rim extending along a plane normal to the longitudinal axis of the shell, is preferred for practical reasons but is not believed to be critical for achieving a sealing connection between the parts. An annular shoulder 105 extends about the shell's lower end $E_2$ and serves to effect a sealing connection with an annular flange 119 of liner 11 but, again, the outward extension of that shoulder, as shown most clearly in FIG. 2, is not believed critical for purposes of producing an effective seal with the flange.

The annular shoulder 105 performs the dual functions of providing an abutment with the annular flange 119 near the lower end of the liner (directly above the one-way valve 13) for a sealing yet easily mountable and de-mountable connection with shell 10, and also providing an easily separable and attachable connection (e.g., in the manner of a snap-on/snap-off connection) with the second connecting means 12 which, in turn, serves to connect the suction bell 1 with milk connecting means 19 in the form of a threaded-necked bottle as depicted in broken lines in FIG. 1.

The shell has a cylindrical body portion 106 provided with a connector 16 which is attachable by a flexible hose (not shown) to an electrically- or manually-operated pump or other source of a cyclic sub-atmospheric pressure or suction (not shown). Under normal conditions, when no suction is applied within shell 10 via connector 16, outer surface 112 of liner 11 is spaced from inner surface 102 of cylindrical body portion 106 of shell 10 to define an inter-space 15, that is, a space closed to ambient conditions and communicating only with a source of cyclic sub-atmospheric air pressure. When atmospheric pressure within inter-space 15 is reduced, for example, to about half its normal value or less, liner 11 will be pulled outwardly in the direction of the arrows towards the inner surface 102 of the shell until the inter-space vanishes and the outer surface 112 of the liner contacts the inner surface 102 of the shell.

It is to be remembered that an essential object of the invention is to simulate the suckling action of a nursing infant. Normally, the suckling effect of palate and mouth of a baby will cause both nipple compression and nipple tension, depending upon the baby's temper and moods as well as upon his or her specific ways of suckling in terms of suckling strength, rhythm, and rate. Accordingly, the action of the suction bell provided by this invention aims to mimic the lips, mouth or oral cavity of a baby leading to an increased suction stimulus and consequently to an increased flow and volume of milk production.

The success of such imitation depends on two main factors: the cycling rhythm of the pump (cycle length and strength), on one hand, and the interaction between the suction bell and a mother's breast, on the other. In contrast to prior art breast pumps where simulation of a suckling baby has been based primarily on the effects of pressure changes acting axially relative to the nipple, the suction bell according to the present invention provides for tensional effects in axial directions relative to the nipple, combined with radially-acting effects of pressure variation. Tensional effects include alternating small elongation and release movements in axial directions. These effects are believed to be due, in part at least, to the specific shape and motion of liner 11, which is substantially coaxial with shell 10, as it moves from the position or condition shown in FIG. 1 to one in which the liner, because of pressure reduction within inter-space 15, has its outer surface 112 in contact with the inner surface 102 of the shell.

To enhance simulation of the suckling action, and to insure a good seal with the breast without sticking to the skin, conical upper portion 111 of the liner is provided with a structured or corrugated surface 115 having alternating ridges or ribs 117 and valleys 118. It has been found that such a corrugated surface and the alternating stretching and contraction of the liner's upper portion in response to pressure changes produces a glissando-like effect that is believed to be stimulative for enhancing milk flow and its production. Such glissando-like action occurs in a smooth, continuous, and alternating manner as pressure diminishes and increases and as the coaxial ridges or ribs in contact with the breast tend to vary in their force of contact and move slightly towards and away from each other as the liner contracts and stretches. It should be noted that corrugation implies that the thickness of the liner is substantially the same in the ridge and valley portions to provide for smooth elongation when liner 11 is caused to move under the effect of pressure reduction into inter-space 15. Typically, the length of the entire corrugated portion of the liner is in the range of about 20 to 50 mm, preferably between about 25 and 40 mm, with ridge portions 117 and valley portions 118 having substantially the same width in the range of about 3 to about 6 mm, preferably about 4 to about 5 mm.

In this context, it is to be noted that length $L_1$ of the corrugated and conical upper portion 111 of the liner exceeds $L_2$ of the conical top portion 101 of the shell. In consequence, transition from conical upper portion 111 of liner 11 to its elongated tubular portion 116 will closely imitate the lips of a suckling baby when the volume of inter-space 15 is repetiously reduced to zero by reason of suction applied through connecting means 16.

The liner 11, including its one-way valve 13, is formed integrally of a soft, resilient elastomer. While any of a variety of natural and synthetic rubber materials might be used, a particularly effective material is believed to be silicone rubber of the type obtainable from reactive organo siloxane compounds, polymerized and cured to provide a physiologically safe and translucent or transparent material that can be sterilized in hot air, water, or steam at temperatures that typically range from 95 to 120° C. Preferred silicone elastomers have a durometer value on the Shore A scale of about 30 to about 55, a tensile strength from about 6 to about 12 Newtons (N) per square millimeter, an elongation at break of from about 500 to 800%, and a residual stress rating under constant deflection of not more than about 35% when tested after 22 hours at 175° C., all values measured by standard testing methods as specified, for example, in German Standards DIN 53504 (March 1985) and DIN 53517 (January 1972). An example of such a material is silicone rubber of the LSR type available from Bayer AG, Leverkusen, Germany, preferably one of the softer materials, such as LSR 2040.

In a preferred embodiment, the liner should have a wall thickness in an unstretched state in the range of about 0.05 to about 1 mm (typically about 0.3 to about 0.4 mm) and can be maintained in a stretched and tensioned state (and effective for sealing) by a force in the range of about 0.4 to about 3N (typically about 0.6 to about 1.2N).

The rigid shell 11 may be formed from any of a variety of strong, durable heat-sterilizable materials. Commerically-available mineral and organic glasses, including acrylic and/or styrene resins, such as ABS-type resins, or polycarbonates, are typical examples of materials suitable for fabricating the rigid shell.

The relationship between the cylinderical body portion 106 of shell 10 and the tubular portion 112 of the liner, which together define inter-space 15, may be further described in a preferred embodiment of the invention as follows: a first and total volume of space is defined within the cylindrical body portion of the shell while a second and partial volume is defined within the tubular portion of the liner when the pressure within the cylindrical body portion of the shell is at ambient or atmospheric pressure. Under such conditions, the second volume amounts to about 20% to about 60% of the first and total volume. Both the shape and the mechanical properties of the liner can easily be selected such that the second volume will increase to about 100% of the first and total volume when pressure is reduced, typically by about 50%. In this manner, it is assured that a predefined maximum suction applied to the breast will not be exceeded because the maximum expansion of the elastic liner is limited by the rigid shell and because sub-atmospheric pressure is not applied directly within the liner and, hence, does not have a direct impact upon the breast.

When assembling the shell 10 and liner 11, the lower end of the deformable liner is pushed downwardly through the conical top portion of the shell and through the shell's lower opening defined by annular shoulder 105 until the resilient annular flange 119 passes through the opening and may be drawn upwardly into sealing contact with shoulder 105. Flange 119 is larger in diameter than the opening defined by shoulder 105, as shown most clearly in FIG. 2, but insertion of the flange through the opening may be readily accomplished not only because of the softness and deformability of the elastic material from which the liner is formed but also because of the downward and inward slope of the frustoconical outer surface 118 of the flange. After the flange is generally in the position shown in FIG. 2, the liner 11 is stretched upwardly and its peripheral lip 114 is pulled over rim 109 at the upper end of the shell. Since the distance between rim 109 and shoulder 105 exceeds the length of the liner (in an unstretched state) measured between lip 114 and flange 119, the elastomeric liner is in an axially stretched and tensioned condition when the parts are assembled as depicted in FIG. 1. It is believed to be an essential feature of the suction bell assembly that liner 11 be maintained in such a tensioned state, with lip 114 and flange 119 held in sealingly engagement with rim 109 and shoulder 105, respectively, to prevent exposure of milk to the air flowing into and out of inter-space 15 through connecting means 16.

Connecting member 12 serves to connect shell 10 with a milk-collecting receptacle (bottle) and represents a second connection means. Member 12 is designed to provide a releasable snap-on/snap-off connection for easy assembly and disassembly before and after use, and for intermediate sterilization, typically by immersion in boiling water. The snap-on/snap-off connection may be effected, for example, by means of a socket 104 capable of receiving and releasably holding the lower end 105 of shell 10. The socket may be integrally molded with a threaded cap 121 for connection to milk bottle 19.

As shown in FIGS. 1 and 2, the one-way valve 13 extends downwardly below flange 119 and shoulder 105 and is therefore not subject to the tension applied to liner 11 when the parts are fully assembled. The valve has a rounded or calotte-shaped lower end portion 131 with such portion being of increased wall thickness as shown most clearly in FIG. 2. At least one slit 28 extends in a diametric plane through the wall and constitutes the valve opening. While the slit might be formed in a separate cutting operation after the liner is molded, it is advantageous, particularly in terms of production and product costs, to form the slit as part of the molding step. While the surfaces defining such a molded slit would be spaced slightly apart when the valve is in a relaxed state, the valve's operation is not adversely effected because only the slightest negative pressure within the liner (resulting indirectly from a reduction in pressure in inter-space 15) is needed to insure valve closure.

Referring to FIGS. 2 and 2A, it will be observed that the inner and outer portions 28a and 28b of slit 28 are slightly offset. The extent of the offset does not exceed the width of each of the slit portions, so that when the elastic valve is in the relaxed condition shown in FIG. 2, the two slit portions communicate with each other. Such a construction allows the slit 28 to be formed in a molding operation with the inner slit portion 28a being formed by a projection or protrusion provided by the inside or male mold (not shown) and the outer slit portion 28b being formed by a protrusion provided by the outside or female mold (not shown). In addition to the manufacturing advantages derived from forming the slit in a molding step, slit 28 with its offset portions 28a and 28b is believed to promote effective operation of the one-way valve by contributing to proper alignment of the sealing surfaces and reducing the possibility of valve collapse during a suction phase of a pumping cycle. As negative pressure develops within the cavity 29 of the valve, the surfaces defining the slit move inwardly towards each other and into sealing engagement, as shown in FIG. 2A where the surfaces defining slit portion 28a are in sealing contact with each other. It is to be understood that as negative pressure increases, the surfaces defining slit portion 28b would also be expected to make sealing contact with each other.

When the pressure in inter-space 15 increases during the discharge phase of a pumping cycle, milk collected in valve cavity 29 and in the lower portion of the liner during the suction phase flows downwardly through the open slit 28 and into bottle 19. Of particular importance with respect to valve operation is the fact that the valve, although formed as an integral part of the liner 11, is not subject to the tension applied to the liner because the valve is located below flange 119 and shoulder 105. Hence, the valve is not distorted, and its operation is not adversely affected, by the stretched and tensioned condition of the liner along the major portion of its length above flange 119.

FIG. 3 illustrates, in a partially sectioned side view, another preferred connection between a shell-plus-liner assembly 3 according to the invention. A rounded annular shoulder 305 of shell 310 fits into a correspondingly rounded sleeve 321 having sufficient elasticity to hold the assembly in a given position yet permitting disassembly and re-assembly in the manner of a snap-on/snap-off connection. This enables a swiveling displacement of the suction bell assembly 3 for selecting the most comfortable angle A between a vertically held milk bottle and the longitudinal axis of the suction bell. For optimal comfort and effectiveness of operation, the central axis of a mother's breast through the nipple should coincide, in essence, with the longitudinal axis of the suction bell.

Socket 321 is integrally molded with a threaded cap 32 for connection with a correspondingly threaded milk bottle (not shown). Liner 311 is held in sealing engagement by means of a resilient outer flange 319, and one-way valve 13, which may be identical to valve 13 described above, protrudes into socket 321 of connector 32.

FIGS. 4, 4A, 5, and 5A illustrate a further embodiment of a one-way valve 43 for use in the suction bell assembly of this invention. As disclosed in previous embodiments, the valve 43 is an integral part of the soft, flexible and elastic liner 11. The essential difference between valve 43 and valve 13 lies in the fact that valve 43 has a pair of crossed slits 438 and 439 rather than only a single slit 28. The provision of crossed slits is believed advantageous because the pressure differential required for valve operation is reduced and the size of the opening for allowing milk to flow into the bottle is increased.

Figure 4:
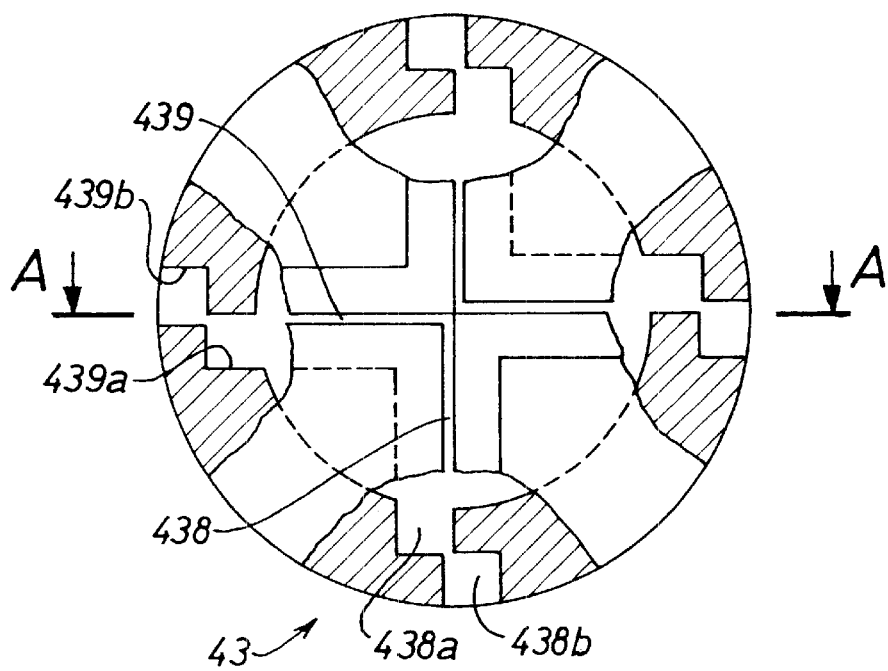
FIG. 4 is a partially-sectioned bottom view of another embodiment of the one-way valve.
Figure 4A:
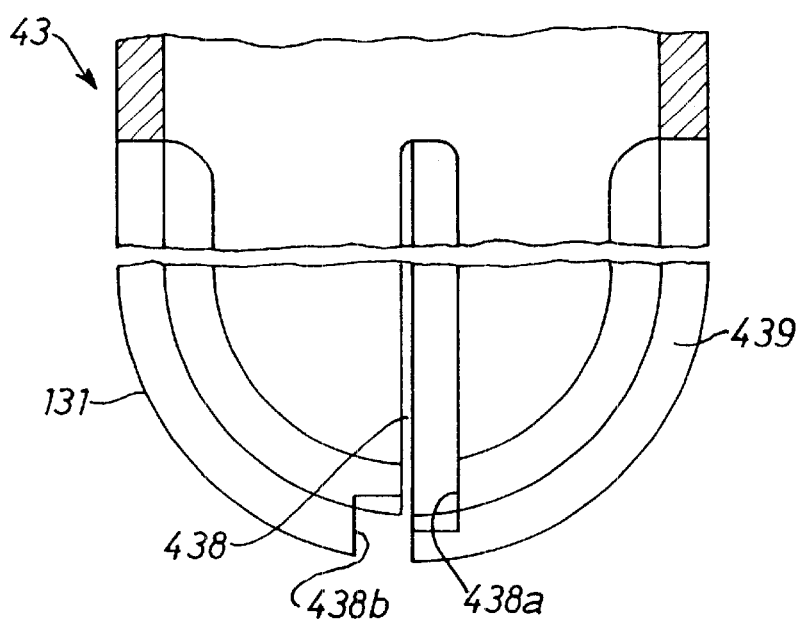
FIG. 4A is a sectional view of the valve shown in FIG. 4.
Figure 5:
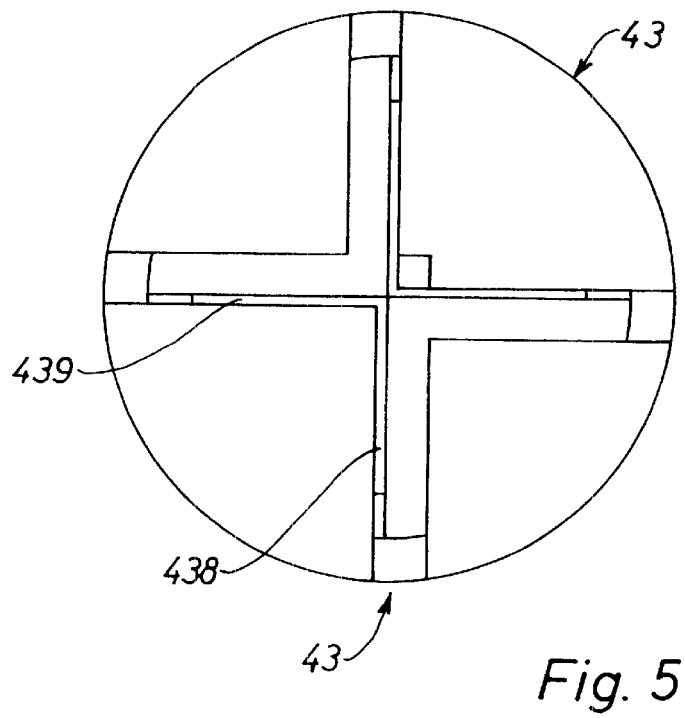
FIG. 5 is a bottom view of the valve shown in FIG. 5 when in open or as-molded position.
Figure 5A:
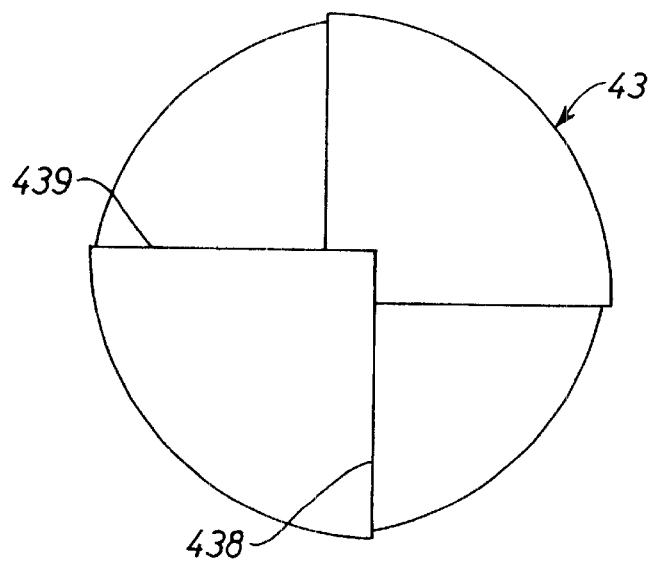
FIG. 5A is a bottom view of the valve of FIG. 5 when the valve is in its closed condition.

Like valve 13, valve 43 preferably has its slits 438 and 439 formed at the time the valve and the liner of which it is a part are molded. For reasons described in connection with the previous embodiments, each slit 438 and 439 is provided with inner and outer offset portions 438a, 438b and 439a, 439b, respectively. As shown in FIG. 4, the extent of offset is slight and does not exceed the width of each of the slit portions. Thus, slit portion 438a communicates with portion 438b with the two portions together forming a slit extending generally along a diametric plane through the wall of the calotte-shaped end portion of the valve. The same observation applies to the offset portions 439a and 439b of slit 439 and, as shown in the drawings, the two crossed slits extend generally along diametric planes that are perpendicular to each other.

When operating a suction bell according to the invention, the source of cyclic sub-atmospheric pressure should be such that the cycle times of between about 0.5 to about 2 cycles per second (i.e., about 30 to about 120 cycles per minute) can be selected by the user, preferably also providing the user with control over the degree of such, typically between about minus 50 mbar to about minus 950 mbar.

Various modifications of shapes, dimensions, materials and methods of controlling the embodiments described herein will be apparent to those skilled in the art within the scope of this invention. For example, while an electrically-operated pump, such as a battery-operated pump, would present a preferred way of operating a suction bell according to the invention, any manually operable source capable of acting as a source of cyclic sub-atmosheric pressure could also be used. Conventional bellows or other devices of any form and material for easy single-handed operation are mentioned by way of example.

Thus, while various exemplary embodiments of the invention have been illustrated and explained, the scope of the patent is intended not to be limited by these examples and is to be construed from the subsequent claims.

What is claimed is:

1. A suction bell for a breast pump, said bell comprising:
   a rigid outer shell having, in axial direction, a substantially Y-shaped cross section and comprising
      a conical top portion having an open upper end and a cylindrical body portion having an inner surface and an open lower end;
         said conical top portion having an outwardly extending rim at said upper end;
         said cylindrical body portion having a first connecting means for connecting said shell with a source of a cyclic sub-atmospheric pressure, an annular shoulder extending about said lower end, and second connecting means for connecting said shell with a milk collecting means; and
   a thin, flexible, and elastic liner having a conical upper portion disposed within said conical top portion of said shell and provided with a peripheral lip sealingly engaging said rim;
   an elongated tubular portion extending through the shell's cylindrical body portion and having an outer surface spaced inwardly from the shell's inner surface when a pressure within said cylindrical body portion of said shell is ambient atmospheric;
      said tubular portion of said liner including a resilient annular flange sealingly engaging said shoulder of said shell and maintaining said liner in an axially stretched and tensioned state; and integral one-way valve means provided by said liner at said lower end of said tubular portion below said shoulder of said shell.

2. The suction bell of claim 1 wherein said valve means comprises a calotte-shaped closure portion at said lower end of said tubular portion of said liner, and said closure portion being provided with at least one slit to permit passage of milk through said lower end of said liner.

3. The suction bell of claims 1 or 2 wherein said valve is located downstream of said resilient annular flange.

4. The suction bell of claim 2 in which said slit extends through a wall of said calotte-shaped closure portion and has offset but communicating inner and outer portions for a flow of milk therethrough.

5. The suction bell of claim 4 wherein said portions of each slit are offset to an extent not exceeding the width of each of said slit portions.

6. The suction bell of claim 4 wherein said valve means is provided with a pair of mutually cross slits.

7. The suction bell of claims 1 or 2 wherein said conical upper portion of said liner is provided with a plurality of coaxially arranged corrugations.

8. The suction bell of claims 1 or 2 wherein a first and total volume is defined within said cylindrical body portion of said shell, and a second and partial volume is defined within said tubular portion of said liner when a pressure within said cylindrical body portion of said shell is ambient atmospheric pressure; and wherein said second volume amounts to about 20 to about 60% of said first and total volume.

9. The suction bell of claim 8 wherein said second volume will increase to about 100% of said first and total volume when said ambient atmospheric pressure is reduced by about 50%.

10. The suction bell of claims 1 or 2 wherein said liner is made of a silicone polymer having a durometer value on a Shore A scale of about 40.

11. The suction bell of claims 1 or 2 wherein said liner has a normal wall thickness in a range from about 0.2 to about 0.5 mm and is maintained in an axially stretched and tensioned state by a force in a range from about 0.4 to about 3N.

12. The suction bell of claim 11, wherein the range of the normal wall thickness of the liner is from about 0.3 to about 0.4 mm.

13. The suction bell of claim 11, wherein the range of said force by which the liner is maintained in the axially stretched and tensioned state is from about 0.6 to about 1.2N.

14. The suction bell of claims 1 or 2 wherein said shell has an annular shoulder providing a curved outer surface fitting into a corresponding sleeve portion on said second connecting means for a swiveling connection between said suction bell and said second connecting means, said connection facilitating mounting and dismounting of said swiveling connection.

15. A liner for a breast pump of the type having an essentially funnel-shaped rigid suction bell with a breast-receiving open upper end and a lower end for connection with a milk collecting means; said liner being made of a thin, flexible, and elastic material and having
   a conical upper portion with an upwardly facing opening and an elongated tubular lower portion, said portions together defining a flow passage through said liner;
      said conical upper portion having a sealing lip extending about said opening for a sealing connection with said breast-receiving upper end of said funnel-shaped rigid suction bell; a resilient external annular flange at said tubular lower portion for a sealing connection with said lower end of said suction bell; and an integral one-way valve at said lower end of said elongated tubular portion of said liner for allowing flow therethrough only in a direction out of said tubular lower portion during suction bell operation.

16. The liner of claim 13 wherein said one-way valve includes a calotte-shaped closure portion at said lower end of said tubular portion of said liner, said closure portion being provided with at least one slit to permit passage of milk through said lower end of said liner.

17. The liner of claims 15 or 16 wherein said one-way valve is provided downstream of said resilient annular flange and said liner is axially stretched and tensioned between said flange and said sealing lip.

18. The liner of claims 15 or 16 wherein said conical upper portion is provided with a plurality of coaxially arranged corrugations.

19. The liner of claims 15 or 16 wherein said liner is made of a silicone polymer having a durometer value on a Shore A scale of about 40.

20. A liner for a breast pump of the type having an essentially funnel-shaped rigid suction bell with a breast-receiving open upper end and a lower end for connection with a milk collecting means; said liner being made of a thin, flexible, and elastic material and having

- a conical upper portion with an upwardly facing opening and an elongated tubular lower portion, said portions together defining a flow passage through said liner;
- said conical upper portion having a sealing lip extending about said opening for a sealing connection with said breast-receiving upper end of said funnel-shaped rigid suction bell; a resilient external annular flange at said tubular lower portion for a sealing connection with said lower end of said suction bell; and an integral one-way valve at said lower end of said elongated tubular portion of said liner for allowing flow therethrough only in a direction out of said tubular lower portion during suction bell operation, said one-way valve including a calotte-shaped closure portion at said lower end of said tubular portion of said liner, said closure portion being provided with a pair of mutually crossed slits to permit passage of milk through said lower end of said liner; and
- said one-way valve being provided downstream of said resilient annular flange.

21. The liner of claim 20, in which each said slit extends through the wall of said calotte-shaped closure portion and has offset but communicating inner and outer portions for a flow of milk therethrough.

22. The liner of claim 21 wherein said portions of each slit are respectively offset to an extent not exceeding the width of each said slit portion.

* * * * *